United States Patent [19]

Turner et al.

[11] 3,950,518

[45] Apr. 13, 1976

[54] HYPOGLYCEMIC COMPOSITION AND METHOD OF USE

[75] Inventors: Carlton E. Turner; John C. Craig, Jr., both of Oxford, Miss.

[73] Assignee: The University of Mississippi, University, Miss.

[22] Filed: May 20, 1975

[21] Appl. No.: 578,941

Related U.S. Application Data

[62] Division of Ser. No. 533,347, Dec. 16, 1974, Pat. No. 3,922,263.

[52] U.S. Cl. ............................... 424/180; 424/195
[51] Int. Cl.$^2$ ................. A61K 31/70; A61K 35/78
[58] Field of Search ................................ 424/180

[56] References Cited
OTHER PUBLICATIONS

Chemical Abstracts Vol. 31: 6734$_9$; Vol. 37: 6343$_8$ and Vol. 40: 6759$_2$.

*Primary Examiner*—Donald B. Moyer
*Attorney, Agent, or Firm*—Laurence, Stokes & Neilan

[57] ABSTRACT

A compound prepared from the extract of *Xanthium strumarium* (cockleburr) characterized by being a white crystalline glycoside having a decomposition point of 278°–279°C.; a molecular formula of $C_{31}H_{48}O_{24}S_2$, the aglycone portion of the molecule having a molecular formula of $C_{19}H_{28}O_4$; substantially no ultraviolet absorption above 200 m$\mu$; infrared spectrum showing hydrogen bonded OH absorption, 3440 cm$^{-1}$; C—H stretch, 2940 cm$^{-1}$; carbonyl stretch, 1735 cm$^{-1}$; C—O stretch, 1250 cm$^{-1}$; and other absorptions at 1640; 1460; 1380; 1040; 1000; 900; and 800 cm$^{-1}$; a nuclear magnetic resonance spectrum in deuterium oxide showing a broad absorption at 304, 230, 162, 134, 92 and 58 cps relative to external tetramethylsilane standard; and the mass spectrum of the silylated derivative gives a mass fragment of 952 amu. Hypoglycemic compositions consisting essentially of the foregoing described compound prepared from cockleburrs in admixture with a non-toxic, pharmaceutically-acceptable carrier. A method of reducing blood sugar levels in animals comprising administering a therapeutically effective concentration of the inventive compound in a pharmaceutically suitable carrier intravenously, orally, intraperitoneally and intramuscularly. The method of preparing a hypoglycemic pharmacologically active therapeutic compound from cockleburrs (*Xanthium strumarium*).

2 Claims, No Drawings

HYPOGLYCEMIC COMPOSITION AND METHOD OF USE

This is a division of application Ser. No. 533,347, filed Dec. 16, 1974 now U.S. Pat. No. 3,922,263.

BACKGROUND OF THE INVENTION

Hypoglycemia is by definition an abnormally low blood sugar level and may be induced by an overdose of exogenous insulin and certain synthetically produced drugs. Well known hypoglycemic drugs are the sulfonylureas, e.g. tolbutamide, chlopropamide, acetohexamide, and tolazamide, which are related chemically to the sulfonamides, and the guanidine derivatives, e.g. phenformin. All of the sulfonylureas act in a similar manner, i.e. by stimulating pancreatic insulin release and decreasing the glucose output from the liver. While the mechanism of action of phenformin is unknown, it is known that the compound inhibits mitochondrial respiratory enzyme systems. It is believed that the inhibition of that enzyme system accelerates glycolysis bringing about hypoglycemia by increasing glucose uptake by the peripheral tissues and decreasing hepatic gluconeogenesis.

While the discovery that such synthetically produced chemicals were effective in reducing blood sugar levels and represent an advance in the art in the treatment of mild diabetes, such drugs have several disadvantages in therapeutic use, not the least of which is the increased risk of acute cardiovascular distresses and even death brought about by their use. In any event, physiologically, the known hypoglycemic drugs are not effective in treating diabetic acidosis or in stressful situations such as infection and surgical procedures.

The product of the invention has the potential of overcoming the disadvantages of the synthetically produced hypoglycemic agents by virtue of the fact that the inventive agent is naturally occurring. Moreover, it may be appreciated that cockleburrs commonly occur in all parts of the world and as such provide a relatively inexpensive source of raw material for world wide production of a naturally occurring insulin substitute. One of the principle advantages of the invention is that the product does not produce its results by causing production of insulin by stimulation of the Islets of Langerhans in the pancreas which mechanism of activity has heretofore limited the use of synthetic drugs to the mildest of diabetic conditions.

SUMMARY OF THE INVENTION

The invention comprises the discovery of a naturally occurring compound which exhibits remarkable hypoglycemic properties without the disadvantage of the known synthetic compounds, and a method of preparing such product from cockleburrs (*Xanthium strumarium*). As a therapeutic composition, the inventive compound is admixed with a non-toxic pharmaceutically diluent carrier and may be administered intravenously, intramuscularly, intraperitoneally and orally.

DESCRIPTION OF THE PREFERRED EMBODIMENTS

The compound of the invention is characterized by being a white crystalline glycoside having a decomposition point of 278°–279°C and molecular formula of $C_{31}H_{48}O_{24}S_2$, the aglycone portion of the glycoside has a molecular formula of $C_{19}H_{28}O_4$. Thin layer chromatography on silica gel with ethyl acetate : methyl ethyl ketone : formic acid : water (5:3:1:1) and visualizing with ultraviolet light, iodine vapor, and acidic ceric sulfate indicated a single component. Additionally, thin layer chromatography on silica gel with butanol : acetic acid : ether : water (9:6:3:1) indicated a single component when developed with anisidine in sulfuric acid - ethanol. The compound exhibits substantially no ultraviolet absorption above 200 m$\mu$, and an infrared spectrum showing hydrogen bonded OH absorption, 3440 $cm^{-1}$; C—H stretch, 2940 $cm^{-1}$; carbonyl stretch, 1735 $cm^{-1}$; C—O stretch, 1250 $cm^{-1}$; and other absorptions at 1640; 1460; 1380; 1040; 1000; 900; and 800 $cm^{-1}$.

The nuclear magnetic resonance spectrum in deuterium oxide shows broad absorptions at 304, 230, 162, 134, 92 and 58 cps relative to external tetramethylsilane standard. The mass spectrum of the silylated derivative gives a mass fragment of 952 amu. The molecular weight of the inventive agent as determined in water is 840.

To prepare the compound of the invention whole cockleburrs are ground to a coarse texture. The coarse mixture is initially cleaned of extraneous materials by a succession of extractions with water or solvents having a gradation of polarity, e.g. hexane, chloroform, ethanol and a final extraction with water. It will be understood that numerous solvents may be utilized in the initial cleaning step. Water is, in all cases, the preferred final solvent in the initial cleaning. The initial extraction steps involve, so to speak, the removal of the roughage. The aqueous extract is then successively treated with solvents of decreasing polarity. While in the preferred embodiment solvent systems comprising water with increasing concentrations of absolute ethanol are initially used followed in succession by methanol and a combination of methanol and chloroform, any combination of protic solvents of decreasing polarity and miscible with water would be useful in the practice of the invention. The end point polarity is reached when the polarity of the solvent system being used lies within the range of the polarity of a 5% solution of chloroform in methanol to a 95% solution of chloroform in methanol. The insoluble precipitate obtained from this treatment step is then washed with a solvent system comprising water and a less polar solvent partially miscible in water. In the preferred embodiment the solvent system consists of a saturated solution of tetrahydrofuran in water. In this step the product will be pulled into the top layer of the less polar of the solvent pair. The solvent is evaporated under vacuum leaving the product, a gummy residue. The product is then crystallized by alcoholic trituration. While cold methanol is the preferred crystalization agent, any low boiling alcohol is suitable for use in this step. The product, a white crystalline solid, is recovered by, for example, filtration or centrifugation.

The following examples exemplify the relative simplicity of preparing the compound of the invention and the preparation of the hypoglycemic composition of the invention:

EXAMPLE 1

4.55 kg mature clockleburrs were coarsely ground in a Wiley mill. The coarsely ground mixture was fed into an extraction percolator and successively extracted three times with water on a volume per volume basis. The water extracts were removed under vacuum, combined and the marc discarded, 118 grams of a dark, waxy appearing material was obtained. The waxy material from the initial aqueous extraction was dissolved in 150 ml water. To this solution 350 ml absolute ethanol was added slowly. 34 g of an insoluble precipitate was obtained therefrom which material exhibited no observable biological activity. The solution was evaporated under vacuum to yield 75 g of a dark waxy appearing material which when pharmacologically screened exhibited significant biological activity in mice. The material was dissolved in 150 ml $H_2O$ followed by the addition of 500 ml of absolute ethanol. 19 grams of an insoluble material precipitated therefrom and upon testing exhibited no observable biological activity. The solution containing 55 g dissolved material was then evaporated. The solid material when pharmacologically screened exhibited significant biological activity when injected intraperitoneally in mice. 250 ml methanol was added to the 55 g of material with vigorous stirring. 13 gms of an insoluble dark mass was removed therefrom which material when screened for therapeutic activity exhibited no observable biological activity. The methanolic solution was evaporated under vacuum and 35 g of dark waxy appearing material isolated which when pharmacologically tested in mice exhibited significant biological activity. This active material was dissolved in 200 ml methanol at 50°C. Upon reduction of the solution to room temperature 50 ml chloroform was added. 14 gms of a brown material thereupon precipitated from the solution. Upon being placed in an inert pharmaceutical carrier this material was pharmacologically screened in mice and exhibited significant pharmacological activity. The methanol-chloroform solution was evaporated under vacuum to yield 19.3 grams of a brown gummy residue which was dissolved in 100 ml methanol followed by the addition of 50 ml chloroform to yield 5.9 grams of an insoluble product which upon pharmacological testing exhibited significant biological activity. The 14 gms of insoluble material from the first methanol-chloroform extraction was dissolved in 150 ml $H_2O$ and 300 ml tetrahydrofuran added slowly with swirling to achieve a two phase system. Subsequently an additional 50 ml tetrahydrofuran was added. Tests revealed that the pharmacologically active principal was contained in the top layer of the two phase system. The top layer was subjected to subsequent treatments for further purification with water and tetrahydrofuran in similar manner to the first treatment. The top layer after vacuum evaporation yielded 2.66 g of a brown gummy material. This material was dissolved in 30 ml water and extracted with 20 ml ethyl acetate. The acetate layer exhibited no biological activity and was discarded. The aqueous layer was then evaporated under vacuum to yield 1.6 g brown gummy product which, upon testing, exhibited significant biological activity. 50 ml methanol was added to the gummy material and the mixture triturated yielding 200 mg of the inventive compound in the form of a white crystalline solid. The compound had the following properties:

| Infrared Absorbances | Ultraviolet |
|---|---|
| $(cm^{-1})$ | No absorbance |
| 3440 (OH stretch) | above 200 m |
| 2940 (CH stretch) | |
| 1734 (C=) stretch) | Nuclear Magnetic Resonance |
| 1250 (C-O stretch) | Broad proton absorbances |
| Other Absorbances: | relative to external |
| 1640 | tetramethylsilane |
| 1460 | 304 cps |
| 1380 | 230 cps |

-continued

| | |
|---|---|
| 1040 | 162 cps |
| 1000 | 134 cps |
| 900 | 92 cps |
| 800 | 58 cps |
| Decomposition Point | Mass Spectrum |
| 278°–279°C | Mass Fragment of 952 amu of silyl derivative. |

EXAMPLE II

In accordance with the method of Example I, 10 kg of coarsely ground cockleburrs were extracted in succession with hexane, chloroform, 95% ethanol and water respectively. The extracted dark waxy material was subsequently treated with the solvent system as described in Example I to produce 405 mg of the inventive compound.

EXAMPLE III

Utilizing the identical solvent systems as set out in Example I, 68 kg of cockleburrs were utilized to yield as a final product 2.2 g purified compound having the same physical and chemical properties as the product obtained in Example I.

The activity of the various residues in Examples I, II and III were screened utilizing a primary screening technique, i.e. CNS Toxocological-Pharmacological Screen. The hypoglycemic activity of the inventive compound, prepared in accordance with Examples I, II, and III, was tested using an experimental in vivo technique utilizing dogs, rabbits and rats.

As discussed hereinabove, the compound of the invention has been found to be a potent hypoglycemic agent in mammals offering many advantages over the compounds known in the art. Treatment is preferably by intravenous administration of the compound in a pharmaceutically-acceptable carrier. In the usual case, saline is the carrier. The actual dosage administered will be determined by such generally recognized factors as the glucose level of the patient's blood, body weight and the severity of the condition being treated which, of course, depends upon the individual patient's physical ideosyncrasies and type of hypoglycemic condition. The compound is administered in a non-toxic dosage concentration sufficient to lower the blood glucose level to the desired concentration. With these considerations in mind, the daily dosage for a particular patient can be readily determined in accordance with conventional techniques in the medical arts.

The intravenous preparation utilized in the tests herein was simply prepared by dissolving the inventive compound in distilled water in concentrations dependent upon the particular animal and dosage unit desired. Each of the animals were anesthetized with conventional anesthetics using conventional techniques. Cannulations were performed on each animal as follows: (1) the right femoral artery was cannulated for the withdrawal of blood samples, (2) the right femoral vein was cannulated for the administration of drug, and (3) the left femoral artery cannulated and attached to a Statham Transducer which enabled readings of blood pressure on a Beckman eight-channel Dynograph. EKG chest leads were also attached to each animal. After a 15-minute equilibration period, a pre-drug control blood sample was withdrawn. After another period of equilibration dosage units were administered and blood samples taken at 15, 30, 60, 75, 105 minutes and 4 hours after drug administration. The hypoglycemic activity of the compound as tested is shown in Table 1.

TABLE 1

| Animal | Dosage Unit mg/kg | Time (min.) | % change from control[a] |
|---|---|---|---|
| Rabbit | 1 | 240 | 43 |
| Rat 1 | 2 | 240 | 24 |
| Rat 2 | 2 | 240 | 64 |
| Rat 3 | 2 | 240 | 42 |
| Rat 4 | 2 | 240 | 80 |
| Rat 5 | 5 | 75 | 69 |
| Rat 6 | 5 | 75 | 66 |
| Rat 7[b] | 1 | 75 | 60 |
| Rat 8[b] | 1 | 240 | 80 |
| Rat 9[b] | 1 | 240 | 80 |
| Dog 1 | 1 | 250 | 68 |
| Dog 2 | 1 | 250 | 68 |

[a]Percentage decrease in blood glucose, each animal serves as its own control by measuring the blood glucose of each animal prior to injection of the drug.
[b]Rats 7–9 were pretreated with alloxan prior to administration of the compound.

Although this invention has been described with references to illustrative embodiments thereof, it will be apparent to those skilled in the art that the principles of this invention can be embodied in other forms but within the scope of the claims.

We claim:
1. A hypoglycemic composition consisting essentially of a glycosidic compound prepared from cockleburrs characterized by being in the form of a white crystalline solid having a decomposition point of 278°–279°C.; a molecular formula of $C_{31}H_{48}O_{24}S_2$, the aglycone portion of said molecule having the molecular formula $C_{19}H_{28}O_4$; substantially no ultraviolet absorption above 200 m$\mu$; an infrared spectrum showing a hydrogen bonded OH absorption, 3440 cm$^{-1}$; C—H stretch, 2940 cm$^{-1}$; carbonyl stretch, 1734 cm$^{-1}$; C—O stretch, 1250 cm$^{-1}$ and other absorptions at 1640; 1460; 1380; 1040; 1000; 900; and 800 cm$^{-1}$; the nuclear magnetic resonance spectrum in deuterium oxide shows broad absorption at 304, 230, 162, 134, 92 and 58 cps relative to tetramethylsilane standard; and the mass spectrum of the silyl derivative gives a mass fragment of 952 amu in admixture with a non-toxic pharmaceutically-acceptable carrier.

2. A process for reducing blood sugar in mammals which comprises administering to animals the composition of claim 1 said composition containing said compound in a hypoglycemicly effective concentration.

* * * * *